United States Patent [19]
Esqueda

[11] Patent Number: 4,974,605
[45] Date of Patent: Dec. 4, 1990

[54] FACIAL PROPHYLACTIC

[76] Inventor: Ricardo J. Esqueda, 1962 N. Prospect Ave., 520, Milwaukee, Wis. 53202

[21] Appl. No.: 455,295

[22] Filed: Dec. 22, 1989

Related U.S. Application Data

[63] Continuation of Ser. No. 24,017, Mar. 10, 1987, abandoned.

[51] Int. Cl.$^5$ .............................................. A61F 13/12
[52] U.S. Cl. ................................ 128/857; 128/206.21; 128/918; 128/858; 128/859
[58] Field of Search ....................... 128/206.21, 206.28, 128/857-859, 917, 918, 830, 842, 844, 846; 2/206; D29/7, 8; 119/129, 130; 446/27

[56] References Cited

U.S. PATENT DOCUMENTS

| | | | |
|---|---|---|---|
| 2,591,783 | 4/1952 | Craddock | 604/353 X |
| 2,606,324 | 8/1952 | Mafko | 446/27 X |
| 2,666,206 | 1/1954 | Mafko | 2/206 |
| 3,536,066 | 10/1970 | Ludwig | 128/132 R |
| 3,695,265 | 10/1972 | Breuik | 128/132 R X |
| 3,804,086 | 4/1974 | Agnew | 128/206.28 X |
| 4,121,304 | 10/1978 | Cooper | 2/206 |
| 4,664,104 | 5/1987 | Jaicks | 604/353 X |
| 4,815,456 | 3/1989 | Rubin et al. | 128/830 X |

FOREIGN PATENT DOCUMENTS

| | | | |
|---|---|---|---|
| 353305 | 5/1922 | Fed. Rep. of Germany | 2/206 |
| 552231 | 4/1923 | France | 2/206 |

Primary Examiner—Robert A. Hafer
Assistant Examiner—Kevin G. Rooney
Attorney, Agent, or Firm—Carl E. Gulbrandsen

[57] ABSTRACT

A soft and pliable mask for the lower face for the prevention of disease, comprised of a molded mask and straps or bands to hold it in place. Breathing passages are provided. A cavity at the bottom fits around the chin and the top edge may be thicker, or reinforced, to provide close adhesion around the nose.

10 Claims, 1 Drawing Sheet

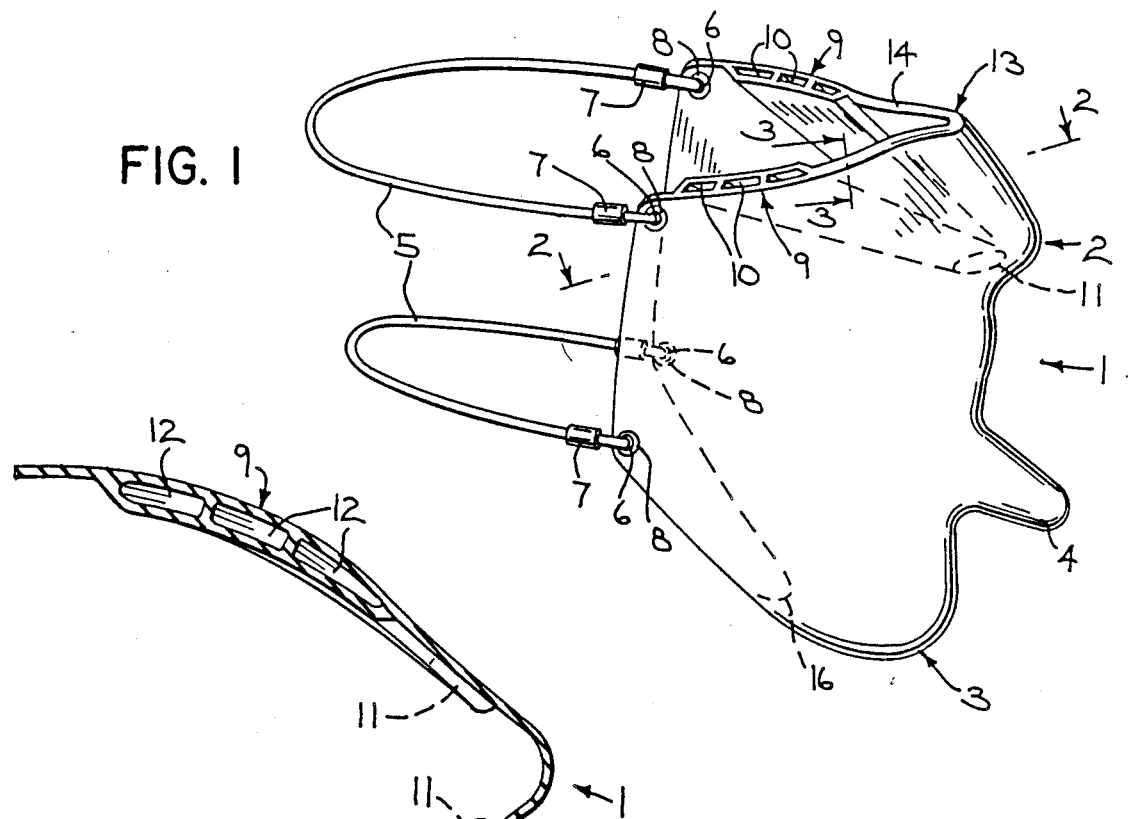
FIG. 1
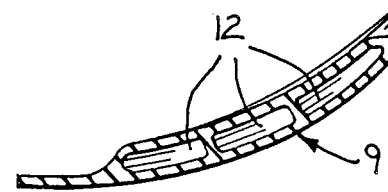
FIG. 2
FIG. 3
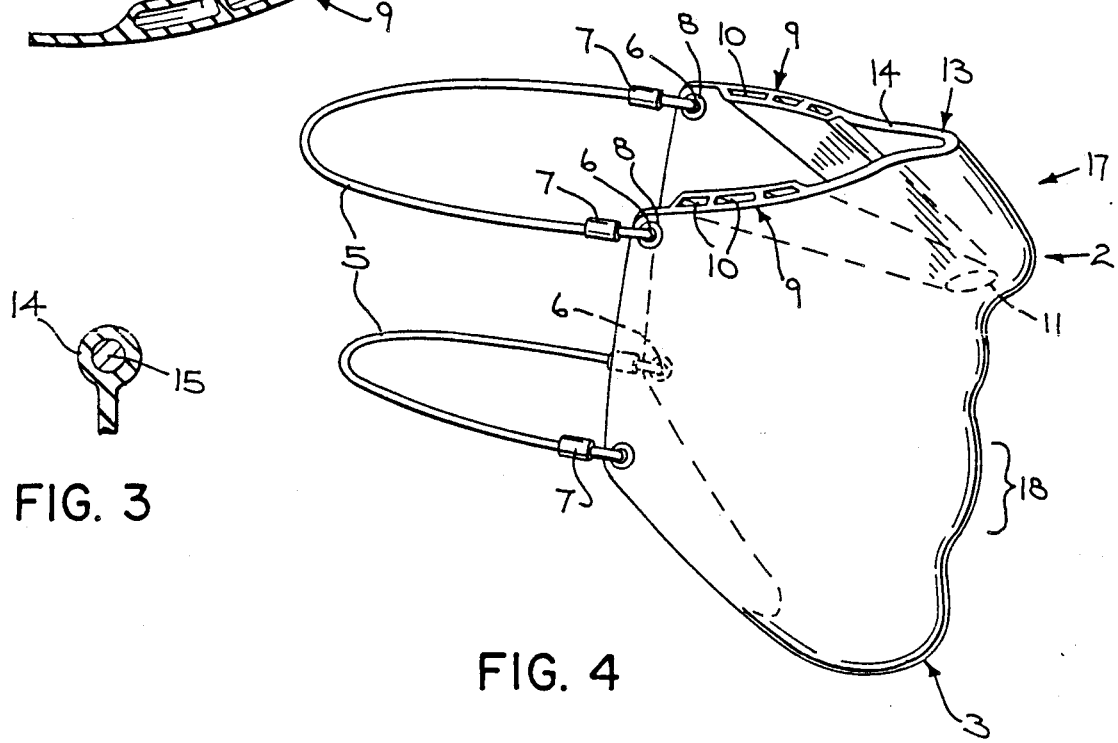
FIG. 4

FACIAL PROPHYLACTIC

This a continuation of copending application(s) Ser. No. 07/024,017 filed on Mar. 10, 1987 now abandoned.

BACKGROUND OF THE INVENTION

This invention relates generally to prophylactics and more specifically to the prevention of the spread of disease through oral sex.

My invention is a safeguard against sexually transmitted diseases, particularly Acquired Immune Deficiency Syndrome (AIDS), or any other such devastating disease.

According to the World Health Organization and the Center for Disease Control, there is no cure for the elusive disease, AIDS. To the best of our knowledge, it can be transmitted in numerous ways during sexual activity. In these modern times, people are more prone to indulge in varied types of sexual activity.

The physical and emotional consequences of contracting AIDS are beyond imagination.

My invention solves the problem of transmitting genital diseases when participating in certain sexual activities.

A further objective of my invention is to alleviate fear and sexual dysfunction, and to put partners at ease during sexual activities.

A further objective of this invention is to provide a comfortable, non-obtrusive prophylactic.

These and other objectives will become apparent when the description is considered in conjunction with the accompanying drawings.

BRIEF DESCRIPTION OF THE DRAWINGS

FIG. 1 is a perspective view of the invention.

FIG. 2 is a cross-sectional view taken along line 2—2 of FIG. 1.

FIG. 3 is a cross-sectional view taken along line 3—3 of FIG. 1.

FIG. 4 is a perspective view of a second embodiment of the invention.

DETAILED DESCRIPTION OF THE INVENTION

Referring to FIG. 1, 1 is the body of the mask. It is formed of latex or a like material and it fits closely to the face. An area 2 fits around the nose and 3 is the part that fits snugly under the chin. A protuberance 4 accommodates the tongue.

The mask is held closely to the face by elastic straps 5 which go around the head. Each strap is affixed to the mask by looping the ends through openings 6 and clamping with parts 7. The openings may be made by grommets 8 but this is not absolutely necessary.

The straps may be elastic as shown, or ties, or bands with buckles, or any other convenient and well-known means of attaching a mask to the face.

Referring to FIG. 2, breathing means 9 are provided. Openings 10 communicate with opening 11, one near each nostril, via passages 12 (FIG. 2). The breathing passages may be molded with the body of the mask as shown, or may be a separate tube or tubes fixed to the inside of the mask by adhesive or other means.

In order to provide adequate contact with the face, the upper front part of the mask, 13 which crosses the bridge of the nose and the front of the face, may be provided with a thicker edge 14 and/or a wire or similar insert 15, as shown in FIG. 3. The insert may be of a formable material such as a soft metal alloy, so as to be able to be conformed to the specific shape of an individual face.

It may be desirable to provide a similar reinforcement at the edge 16 of the chin cavity 3 (FIG. 1).

A second embodiment of the invention is shown in FIG. 4. Here the mask 17 is similar to the first embodiment but is constructed of a latex or the like that is extremely flexible and elastic, so that a front area 18 of the mask does not require a protuberance for the tongue. Since this prophylactic also must fit snugly, it too is provided with breathing openings 10 and passages identical to those shown in FIGS. 1 and 2.

The above description is intended in no way to limit the scope of the invention, but only to serve to demonstrate two of many possible embodiments of the invention.

I claim:

1. A prophylactic for protecting the wearer from the transmission of disease through oral sex, said prophylactic comprising a mask-like member having portions which snugly fit over the nose, mouth and chin of a wearer and protect the lower face of a wearer, said member being imperforate about the nose and mouth and chin portions of said member, said member having a thick bottom edge which fits under the wearer's chin, said member also having breathing passages therein which extend from a peripheral edge of said member to the wearer's nose and means for accommodating the projected tongue of the wearer.

2. The prophylactic of claim 1 in which the means for accommodating the projected tongue of the user is a tongue-receiving protuberance.

3. The prophylactic of claim 1 in which the means for accommodating the projected tongue is an area of extremely flexible and elastic material which will stretch outwardly to accommodate a projected tongue.

4. The prophylactic of claim 1 wherein, said thick top edge and said thick bottom edge have means for conforming said top edge and bottom edge to the shape of said wearers face.

5. The prophylactic of claim 4 wherein, said means for conforming is a soft metal-like insert.

6. A prophylactic face mask, comprising:
   a. a member adapted to fit snugly over at least the lower portion of a human face, said member having a portion adapted to cover said human's nose and another portion adapted to cover said human's mouth, said portion and other portion being imperforate, said member being formed of a flexible latex-like material;
   b. a means for attaching said member to said human's face whereby said member fits snugly against said human's face;
   c. a breathing passage in said member which communicates air from a peripheral edge of said member to said human's nose;
   d. a means whereby with said member snugly attached to said human's face said other portion permits full extension of said human's tongue so as to touch another human with said tongue without making actual dermal contact between said tongue and said other human.

7. A prophylactic face mask as claimed in claim 6, wherein said means for attaching said member to said human's face includes at least two elastic straps.

8. A prophylactic face mask as claimed in claim 6, wherein said breathing means comprises breathing passages molded to the inside surfaces of said member, each said breathing passage having one end open to said peripheral edge and an opposite end open to said wearer's nostril.

9. A prophylactic face mask as claimed in claim 6, wherein said breathing means comprises breathing tubes fixed to the inside surface of said member, each said breathing tube having one end open to said peripheral edge and an opposite end open to said wearer's nostril.

10. A prophylactic face mask as claimed in claim 6, wherein said means for permitting full extension of said human's tongue comprises said portion being a tongue-receiving protuberance.

* * * * *